United States Patent [19]

Louderback et al.

[11] 3,977,995

[45] Aug. 31, 1976

[54] CALIBRATING FLUID FOR BLOOD CELL COUNTING AND HEMOGLOBIN DETERMINATION

[75] Inventors: Allan L. Louderback, Temple City; Anthony J. Fontana, Glendora, both of Calif.

[73] Assignee: Baxter Laboratories, Inc., Deerfield, Ill.

[22] Filed: Oct. 17, 1974

[21] Appl. No.: 515,760

[52] U.S. Cl. .................................. 252/408; 356/39; 356/42; 424/2; 23/230 B
[51] Int. Cl.² .................. G01N 33/16; G01N 31/22
[58] Field of Search .................. 23/230 B; 252/408; 356/39, 42

[56] References Cited
UNITED STATES PATENTS

| | | | |
|---|---|---|---|
| 3,558,522 | 1/1971 | Louderback | 23/230 B |
| 3,574,137 | 4/1971 | Decasperis | 23/230 B |
| 3,629,142 | 12/1971 | Marbach | 23/230 B |
| 3,640,896 | 2/1972 | Decasperis | 23/230 B |
| 3,705,110 | 12/1972 | Louderback | 252/408 |
| 3,728,226 | 4/1973 | Louderback | 23/230 B |
| 3,751,381 | 8/1973 | Megraw | 23/230 B |
| 3,859,049 | 1/1975 | Ware | 23/230 B |

*Primary Examiner*—Morris O. Wolk
*Assistant Examiner*—Sidney Marantz
*Attorney, Agent, or Firm*—Louis Altman; Lawrence W. Flynn; Max D. Hensley

[57] ABSTRACT

A calibrating fluid for automated instruments for blood cell counting and hemoglobin determination comprising a sterile solution of oxyhemoglobin or other derivative products of hemoglobin and containing latex particles.

3 Claims, No Drawings

CALIBRATING FLUID FOR BLOOD CELL COUNTING AND HEMOGLOBIN DETERMINATION

BACKGROUND OF THE INVENTION

This invention relates to a calibrating fluid for automated blood cell counting instruments.

The use of automated blood cell counting instruments in hematology is well known. In general, these instruments employ one or the other of two types of particle size analyses. In one type, each particle is counted and its discrimination property is measured directly. In the other type, the particles are measured in bulk and particle behavior is recorded through a series of measurements of the magnitude of the bulk, in terms of the count, combined surface area or combined mass. The type of measurement used then determines the basis of the size distribution.

Optical and electrical properties are two of the most prevalent types of size discriminating properties employed in these particle size analysis instruments. The optical equipment generally employs imaging, spectral transmission, scattering and diffraction mechanisms, while the electrical equipment usually employs resistance, capacitance, and charge mechanisms.

In addition to the counting of blood cells, the more sophisticated automated blood cell counting instruments provide determinations of other blood values such as hematocrit and hemoglobin values. Because of its characteristic red color, hemoglobin lends itself to colorimetric determinations. This gives rise to the use of a colorimeter unit on various blood cell counting instruments.

Various methods of hemoglobin determination which are generally employed in these automated instruments are the cyanomethemoglobin technique and the oxyhemoglobin method. In the former technique, the blood specimen is diluted with a reagent containing ferricyanide and cyanide, which converts both reduced hemoglobin and oxyhemoglobin to the cyanomethemoglobin form. The absorbance of the cyanomethemoglobin at 540 m$\mu$ is then used for quantitation. In the latter method, the blood specimen is diluted with an aqueous solution tetrasodium salt of ethylenediamine tetraacetic acid (EDTA) and mixed with air to convert hemoglobin to oxyhemoglobin. The absorbance of oxyhemoglobin at 540 m$\mu$ is then measured.

Notwithstanding the general reliability of commercially available automated blood cell counting instruments, test values obtained with these instruments are only as accurate as the operator's technique and understanding of the instrument. In the absence of stringent control programs, together with regular recalibration of the instruments, one cannot always be assured of correct results. Experience has shown that quality control in the application and use of these automated blood cell counting instruments is a necessity for good hematological practice.

In the case of some types of automated blood cell counting instruments, the use of fresh whole blood in calibrating the instrument is a very cumbersome procedure, requiring approximately 2 hours to calibrate the instrument. When using the reference control blood supplied by the manufacturer of these instruments, values recorded under "mean value" in the assay instruction sheet are set on the instrument after the reference control blood has been allowed to cycle through the machine. In other words, values recorded on the reference control blood are used to calibrate the machine. It has been found in these instances that when a hematocrit which has been reported at 47.3, for example, on the assay instruction sheet is actually spun in a centrifuge, it does not give an answer of 47.3, but gives an answer of 27-30. Therefore, the reported value is not a true hematocrit. In reporting the hematocrit values, the numbers are given with reference to the specific type of machine used for the determination, which further indicates that this is not a true hematocrit. Thus, the importance of calibrating the machine correctly cannot be overstressed.

Among the reference control blood systems used for calibrating blood cell counting instruments are the semi-fixed systems in which the cells are lightly tanned either with formaldehyde, gluteraldehyde, or tannic acid. By this procedure, the outer membrane of the red blood cell has been fixed so that it cannot swell, although the cell can shrink. If the value which the manufacturer of the blood cell counting machine has placed on the assay instruction sheet is not correct and operators are setting this value into the machine and cycling presently-available calibrating solutions into the machine, it will appear that the calibrating solution has swollen more than is actually the case.

Other known reference control systems for automated blood cell counting instruments are described in U.S. Pats. Nos. 3,558,522; 3,705,110 and references cited therein.

The need for accurate color standards in clinical hemoglobinometry to establish the relation between instrument readings and concentration of hemoglobin in unknown samples is further set forth in various publications, for example, the paper by Cannan, *Amer. J. Clin. Path.*, Vol. 30, pp. 211–215 (1958).

Accordingly, it is an object of this invention to provide an improved calibrating fluid for automated blood cell counting instruments.

It is a further object of this invention to provide an improved calibrating fluid for automated instruments, used for blood cell counting and hemoglobin determinations.

Other objects and advantages of the invention will be apparent to the person skilled in the art after reading the present specification and the appended claims.

SUMMARY OF THE INVENTION

A calibrating fluid for automated blood counting instruments has now been developed which is essentially a sterile solution of oxyhemoglobin or other hemoglobin derivative products containing latex particles. These hemoglobin derivative products can be oxyhemoglobin, oxazohemoglobin, methemoglobin, cyanomethemoglobin, carboxyhemoglobin, sulfhemoglobin, ferrihemoglobin, ferrohemoglobin and similar such derivative products. They are employed in the calibrating fluid at a concentration of from about 12 to about 20 grams per ml. on a hemoglobin basis. The latex particles have a particle size of from about 5 to about 20 microns and are employed in the calibrating fluid at a concentration of from about 8,000 to 22,000.

To calibrate a blood cell counting machine with the calibrating fluid of the present invention, the operator first draws fresh blood from a non-smoker into an EDTA Vacutainer (trademark of Becton, Dickinson and Co.) tube. This fluid blood sample is well mixed and counted either by hand or by a calibrated blood counting machine, to ensure that the counts for the red blood cells and the white blood cells (using a lysing agent for the white blood cell count) are correctly established. Manual hemoglobins and hematocrits are then performed on this blood sample. When all four of these parameters are known, the other three parameters, mean corpuscular volume (MCV), mean corpuscular hemoglobin concentration (MCHC), and mean corpuscular hemoglobin (MCH) can be calculated from these earlier parameters. The operator next draws this primary standardizing blood into the blood counting machine and sets the machine to the values obtained from the aforesaid counts and calculations. The machine is now properly standardized against procedures which can be carried out by hand in the laboratory to verify the values obtained.

After this primary standardization, the operator then cycles the calibrating fluid of this invention through the machine and records the values obtained as a result of these measurements. Values are thus obtained for the calibrating fluid of the present invention which makes it a secondary standard for the machine.

To calibrate the machine daily, the operator pours the calibrating fluid of the present invention into the machine and sets the machine according to the values obtained after the primary standardization. The secondary standard then eliminates the immediate problem of carrying out the primary standardization every day and gives reliable results based on the electronics of the machine. The secondary standardization can easily be completed in ten minutes each day to be in conformance with the primary standard. Because the machines vary from day to day in some of their values, they should be set every day. By using the secondary standard on the machine, one can cycle the calibrating fluid into the machine and use this solution in the manner for which it is designed, that is, as a control product to be read once, twice, or several times a day, to ensure that the machine is operating properly and within certain limits of coefficient of variation for each of the test systems.

DESCRIPTION OF THE PREFERRED EMBODIMENTS

A calibrating solution for automatic blood counting machines such as the Coulter Counter Model S, manufactured by Coulter Diagnostics, Inc. of Hialiah, Florida, was made as follows:

Thirty ml. of water was added to 10 ml. of semipacked blood cells, and the mixture was stirred for 1 hour. This caused the complete lysis of the blood cells in the hypotonic solution.

The above solution was then filtered through a prefilter, and through 1.2, 0.45, and 0.22 micron sterile filtration systems. Fifteen ml. of this concentrated solution was added to 500 ml. of isotonic diluent containing sodium azide preservative. This solution was diluted in isotonic diluent because when used in the blood counting machine it must have the same conductivity as the regular isotonic diluent employed therein. At this point, the product was an oxyazohemoglobin.

The concentration of the solution was then adjusted by dilution at 540 nm to vary between 600 and 720 milli O. D. units (0.600 – 0.720).

Then, 100 $\mu$l of latex* solution was added to 500 ml. of the diluted oxyazohemoglobin, and mixed well. The latex solution, which is the one conventionally used in control blood for automated instruments, was previously sterilized in an autoclave.

*The concentration of the latex by assay was as follows: Ten $\mu$l of the concentrated material was added to 100 ml. of isotonic diluent, and a count of approximately 44,248 × 10$^9$ counts per ml. of the concentrate was obtained. (one $\mu$l = one mm$^3$)

The synthetic latex particles used in this invention are generally spherical in shape, they have a relatively uniform size of from about 5 to about 20 microns, which approximates the relative size of the normal leukocytes, or white cells, and are preferably employed in the calibrating fluid at a concentration of from about 8,000 to about 22,000 particles per cubic millimeter. In the calibration of blood cell counting apparatus, it is preferred to use these elevated levels of particles which stimulate the white cells to provide greater accuracy at the lower end of the curve for average white cell counts. The most preferred average particle count is about 16,000 particles per cubic millimeter.

These latex particles can comprise polystyrene, polyvinyl toluene, and/or styrene-divinylbenzene copolymer latex and the like synthetic polymeric latex materials of suitable particle size.

The styrene-divinylbenzene copolymer latex particles are preferred for use in this invention. These latex particles are visible under the microscope under conventional magnifications at 10X and 40X, they are inert to the usual red cell lysing agents, such as acetic acid and various detergent substances, and otherwise provide suitable simulation of the white blood cells in the calibrating fluid of this invention. They are available commercially with a particle size ranging from 6 to 18 microns.

Various commercially available instruments are suitable for calibration with the calibrating fluid of this invention. One specific example is the "Coulter Electronic Blood Cell Counter, Model S," and similar such equipment as described, for example, in U.S. Pats. Nos. 2,656,508; 2,869,078; 2,985,830; and 3,340,470. This type of instrument discriminates among particles by how they affect the electrical resistance of the fluid medium containing the particles in suspension as they pass through an orifice.

The calibrating fluid of the present invention is particularly useful for standardizing the Coulter Counter Model S. The calibrating fluid is placed in 10 ml. or other suitable volume into either a plastic vial or glass vial to be utilized in the machine. The aspiration switch is set to 1:224 dilution, as are the various chambers used to cycle the solution into the machine. A final dilution of 1:251 is made by the machine as the Coulter detergent (Lyse S Solution) is added in one of the chambers. When the lysing solution is added to this chamber, it immediately converts the calibrating fluid from the oxyazohemoglobin into a true cyanomethemoglobin, and one can see the original reddish color of this fluid immediately change to the brownish color of cyanomethemoglobin. The optical density of this solution when made into cyanomethemoglobin has been examined, and the 0.660 optical density solution at 540 nm of the oxyhemoglobin solution when converted to cyanomethemoglobin solution gives an optical density of about 0.422. This corresponds in a one cm. cuvette system to a cyanomethemoglobin concentration of approximately 15.2 gm% (gram per ml.) of hemoglobin.

As this diluted solution has been converted into cyanomethemoglobin, it is drawn into the final counting chamber. In this counting chamber, on the right side of the machine, counts are performed for the white blood cell count, and the latex particles are utilized as the white blood cell count material. At the same time, assays are done photometrically for cyanomethemoglobin in this chamber, and thus two results are obtained in this chamber.

The left side of the machine has tubing leading to a graduated cylinder so that when the first and second dilutions are made for this side, the material is drawn off into a waste container. A second vial of calibrating fluid is poured into the left counting chamber for making red blood cell counts, and the synthetic latex particles, which are of a size between 6 and 18 microns, are allowed to pass through the counting orifice. At the same time the machine is counting the number of counts by impedance measurement, it is also measuring the volume displaced as the particles pass through this open orifice. It is thus possible to size the cells at the same time the cells are counted. The latex particles are then able to give a mean cell volume standard value which can be used in setting the machine.

By using the above procedure, the following counts were obtained:

|  | Value | Units |
|---|---|---|
| White blood cell | 17.6 | Thousands per cubic micron ($\mu$l) |
| Red blood cell | 4.65 | Millions per cubic micron ($\mu$l) |
| Hemoglobin | 15.7 | Grams per 100 ml. |
| Hematocrit | 82.4 | Percent |
| MCV | 177.0 | Cubic microns ($\mu^3$) |
| MCH | 33.7 | Micromicrogram, ($\mu\mu$g) |
| MCHC | 18.9 | Percent |

In practice, the final product ranges from about 12 gm% to about 20 gm% of hemoglobin, and preferably from about 13.5% gm% to 17 gm% of hemoglobin.

The calibrating fluid of the present invention was used in the Coulter Counter Model S as follows:

Two 10 ml. containers of the calibrating fluid were selected and mixed well by inverting several times.

The A-1 RBC Mixing Chamber cap of the machine was removed and the blood sample tube disconnected at the mixing chamber junction. The disconnected sample tube end was placed into a container having sufficient height to collect the isotonic diluent which normally dilutes the sample for erythrocytes (RBC) counting.

The entire contents of one calibrating fluid container were poured into the A-2 mixing chamber and the cap was replaced.

The aspirator switch was set to 224/1 DIL. The well-mixed standardizing solution from the second container was introduced through the capillary blood aspirator.

The side opening of the A-2 mixing chamber was blocked by holding a finger over it until the calibrating fluid had passed into the RBC aperture counting bank.

The seven parameters were printed on the print-out card as follows:

|  | Test | Assigned Value | ±2 SD* |
|---|---|---|---|
| Leukocytes | WBC × 10³ | 15.7 | 0.5 |
| Erythrocytes | RBC × 10⁶ | 3.82 | 0.2 |
| Hemoglobin | Hgb gm % | 16.7 | 0.5 |
| Hematocrit | Hct % | 82.6 | 4.0 |
| Mean Corpuscular Volume | MCV $\mu^3$ | 217 | 2 |
| Mean Corpuscular Hemoglobin | MCH $\mu\mu$g | 44.7 | 1.7 |
| Mean Corpuscular Hemoglobin Concentration | MCHC % | 20.4 | 0.7 |

*Variation within 2 standard deviations

Various other examples and modifications of the foregoing examples will be apparent to the person skilled in the art after reading the foregoing specification without departing from the spirit and scope of the invention and it is intended to cover in the appended claims all such examples and modifications.

What is claimed is:

1. A calibrating fluid for automated instruments for blood cell counting and hemoglobin determination which is substantially free from red blood cells and which consists essentially of an aqueous isotonic solution containing therein (A) a solubilized material selected from the group consisting of oxyhemoglobin and other hemoglobin derivative products, said solubilized material obtained by completely lysing red blood cells, filtering and recovering the filtrate, and (B) synthetic latex particles selected from the group consisting of polystyrene, polyvinyltoluene, and styrenedivinylbenzene copolymer with a particle size ranging from about 5 to about 20 microns and in an amount of from about 8,000 to about 20,000 particles per cubic millimeter and in which the concentration of (A) as hemoglobin ranges from about 12 gm% to about 20 gm%.

2. A method for making a calibrating fluid for automated instruments for blood cell counting and hemoglobin determination comprising:

adding about one part of semi-packed blood cells to about three parts of water and stirring for a period of time sufficient to cause complete lysis of the blood cells in the solution;

filtering said solution to obtain a filtrate of solubilized material selected from the group consisting of oxyhemoglobin and other hemoglobin derivative products;

adding about three parts of said filtrate to about 100 parts of isotonic diluent to form a second solution;

adjusting to said third solution a sufficient amount of a solution of synthetic latex particles to provide from about 8,000 to about 22,000 particles of latex per cubic millimeter of solution.

3. The process of claim 2 wherein the solution is successively filtered through 1.2, 0.45 and 0.22 micron porous filters.

* * * * *